(12) United States Patent
Ohama

(10) Patent No.: US 8,810,810 B2
(45) Date of Patent: Aug. 19, 2014

(54) PRINTING QUALITY INSPECTION APPARATUS

(75) Inventor: Kentaro Ohama, Ibaraki (JP)

(73) Assignee: Komori Corporation, Tokyo (JP)

( * ) Notice: Subject to any disclaimer, the term of this patent is extended or adjusted under 35 U.S.C. 154(b) by 139 days.

(21) Appl. No.: 13/224,213

(22) Filed: Sep. 1, 2011

(65) Prior Publication Data

US 2012/0069365 A1  Mar. 22, 2012

(30) Foreign Application Priority Data

Sep. 22, 2010  (JE) ................. 2010-211839
Sep. 22, 2010  (JP) ................. 2010-211842
Sep. 22, 2010  (JP) ................. 2010-211846

(51) Int. Cl.
| | | |
|---|---|---|
| G06K 15/16 | (2006.01) | |
| G06K 9/00 | (2006.01) | |
| B41F 33/00 | (2006.01) | |
| G01N 21/84 | (2006.01) | |
| G01N 21/86 | (2006.01) | |
| G01J 1/42 | (2006.01) | |
| G01J 1/06 | (2006.01) | |

(52) U.S. Cl.
CPC ............ *B41F 33/0036* (2013.01); *G01N 21/84* (2013.01); *G01N 21/86* (2013.01); *G01J 1/4223* (2013.01); *G01J 1/06* (2013.01)
USPC ........................................ 358/1.12

(58) Field of Classification Search
CPC ............................ G06K 15/16; G01N 21/892
USPC ........................................ 358/1.12
See application file for complete search history.

(56) References Cited

FOREIGN PATENT DOCUMENTS

| | | |
|---|---|---|
| CN | 1428245 A | 7/2003 |
| CN | 1619296 A | 5/2005 |
| CN | 2762120 Y | 3/2006 |
| JP | 09-300596 | 11/1997 |
| JP | H11-108635 A | 4/1999 |
| JP | H11-108637 A | 4/1999 |
| JP | 2003-077319 A | 3/2003 |
| JP | 2004-136585 A | 5/2004 |
| JP | 2005-188929 | 7/2005 |
| JP | 2005283233 A | 10/2005 |
| JP | 2006-001079 A | 1/2006 |
| JP | 2010-190821 A | 9/2010 |
| WO | WO 2011/055432 | 5/2011 |

OTHER PUBLICATIONS

Machine translation for JP 2005-188929, IDS.*

* cited by examiner

*Primary Examiner* — Qian Yang
(74) *Attorney, Agent, or Firm* — Blakely Sokoloff Taylor & Zafman

(57) ABSTRACT

This invention discloses a printing quality inspection apparatus including a light irradiation device, an image capture device, a diffusely reflecting plate, and a determination device. When a member to be printed is a first sheet member, light emitted by the light irradiation device is diffusely reflected by the first sheet member and enters the image capture device. When the member to be printed is a second sheet member, the light emitted by the light irradiation device is diffusely reflected by the diffusely reflecting plate, is specularly reflected by the second sheet member, and enters the image capture device.

9 Claims, 11 Drawing Sheets

PRINTING QUALITY INSPECTION APPARATUS

BACKGROUND OF THE INVENTION

The present invention relates to a printing quality inspection apparatus which inspects the printing quality of an image printed on opaque paper such as white paper available as a general printing sheet, vapor deposition paper having undergone a vapor deposition process on its surface, or a transparent film.

In general, opaque paper such as white paper has a diffusely reflecting surface, whereas vapor deposition paper has a specularly reflecting surface. A conventional printing quality inspection apparatus which inspects whether an image printed on such opaque paper or vapor deposition paper is printed in a normal state includes two types of illumination light sources: a dark-field illumination light source and a bright-field illumination light source, as disclosed in Japanese Patent Laid-Open No. 11-108637 (literature 1). When an image of a printing product printed on an opaque printing paper sheet is to be detected by the conventional printing quality inspection apparatus, the dark-field illumination light source is turned on to use dark-field illumination light. On the other hand, when an image printed on vapor deposition paper is to be detected by this printing quality inspection apparatus, both the dark-field illumination light source and the bright-field illumination light source are turned on to use both dark-field illumination light and bright-field illumination light, respectively.

Japanese Patent Laid-Open No. 11-108635 (reference 2) proposes another printing quality inspection apparatus including a light diffusing member which is formed from a translucent material and is provided between an object to be inspected and an illumination light source. In this printing quality inspection apparatus, illumination light emitted by the illumination light source scatters in various directions upon being transmitted through the light diffusing member. The target surface of the object to be inspected is illuminated with the scattered illumination light at a nearly uniform illuminance, and captured by an image capture camera.

In recent years, a transparent film is often used as a printing sheet to print an image on the transparent film. To inspect whether an image is printed on the transparent film in a normal state, the operator extracts printed samples for every predetermined number of sheets, and visually inspects them for a printing failure. Therefore, a heavy burden is inflicted on the operator. Also, when a printing failure occurs in a printing product which is not extracted as a sample, a defective printing product is shipped without being detected. Moreover, even if the operator becomes aware of a printing failure, defective printing products are produced in large quantities, thus wasting printing materials.

In the conventional printing quality inspection apparatus disclosed in literature 1, two types of light sources: dark- and bright-field light sources are necessary, thus leading to an increase in cost. Also, it is necessary to operate a switch for switching the process involved, in accordance with whether a printing product printed on opaque paper or that printed on vapor deposition paper is to be inspected, thus inflicting a heavy burden on the operator. Furthermore, if the operator is unaware of erroneous detection because he or she has forgotten to switch the process involved, large amounts of printing materials are wasted.

On the other hand, in the printing quality inspection apparatus disclosed in literature 2, the light diffusing member is inserted between the object to be inspected and the illumination light source. Therefore, due to a shortage of illumination light which impinges on the target surface, an image printed on transparent paper cannot reliably be detected.

SUMMARY OF THE INVENTION

It is an object of the present invention to provide a printing quality inspection apparatus which can inspect the printing quality of an image printed on opaque paper, vapor deposition paper, or a transparent film with the same configuration.

It is another object of the present invention to provide a printing quality inspection apparatus which reduces the manufacturing cost and prevents the waste of printing materials while relieving the operator's burden.

In order to achieve the above-mentioned object, according to the present invention, there is provided a printing quality inspection apparatus including a light irradiation device which irradiates with light a member to be printed including a first sheet member having an image printed thereon and a diffusely reflecting surface, and a second sheet member having an image printed thereon and a specularly reflecting surface, an image capture device which receives light which is emitted by the light irradiation device and passes through the member to be printed, thereby capturing the image on the member to be printed, a diffusely reflecting plate which is opposed to the light irradiation device on an opposite side of a light incident path defined from the member to be printed to the image capture device, and a determination device which compares an image capture signal output from the image capture device and a reference signal stored in advance to inspect quality of the image printed on the member to be printed, wherein when the member to be printed is the first sheet member, the light emitted by the light irradiation device is diffusely reflected by the first sheet member and enters the image capture device, and when the member to be printed is the second sheet member, the light emitted by the light irradiation device is, after diffusely reflected by the diffusely reflecting plate, specularly reflected by the second sheet member and enters the image capture device.

DESCRIPTION OF THE PREFERRED EMBODIMENTS

A printing quality inspection apparatus according to the first embodiment of the present invention will be described below with reference to the accompanying drawings.

Figure 1:
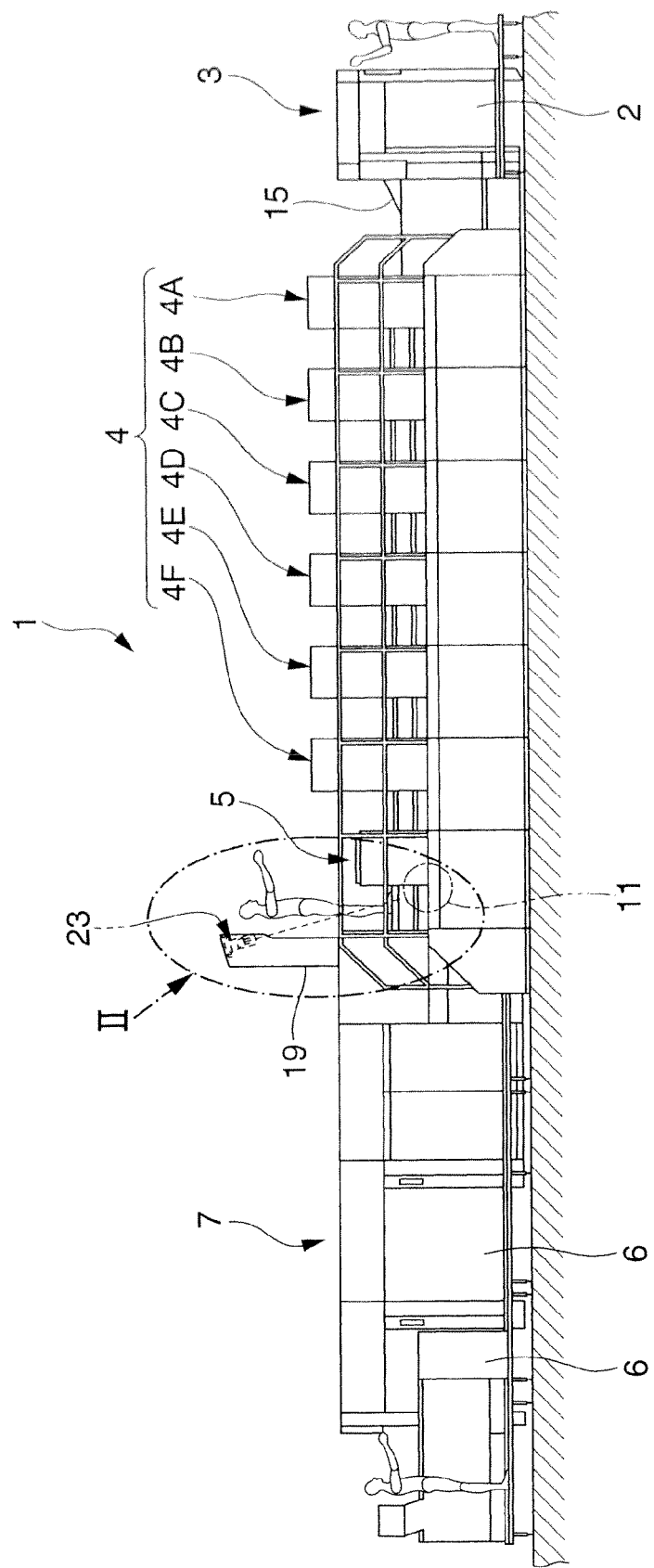
FIG. 1 is a side view of a sheet-fed offset rotary printing press to which a printing quality inspection apparatus according to the present invention is applied.

As sheet-fed offset rotary printing press 1 includes a sheet feeding device 3, printing unit 4, coating unit 5, and sheet delivery device 7, as shown in FIG. 1. The sheet feeding device 3 feeds stacked members to be printed 2 one by one. The printing unit 4 includes six printing units 4A to 4F which print six colors on the member to be printed 2 supplied from the sheet feeding device 3. The coating unit 5 coats varnish on the printing surface of the member to be printed 2 printed by the printing unit 4. The sheet delivery device 7 dries the member to be printed 2 coated by the coating unit 5, and delivers it onto a delivery pile 6.

Figure 2:
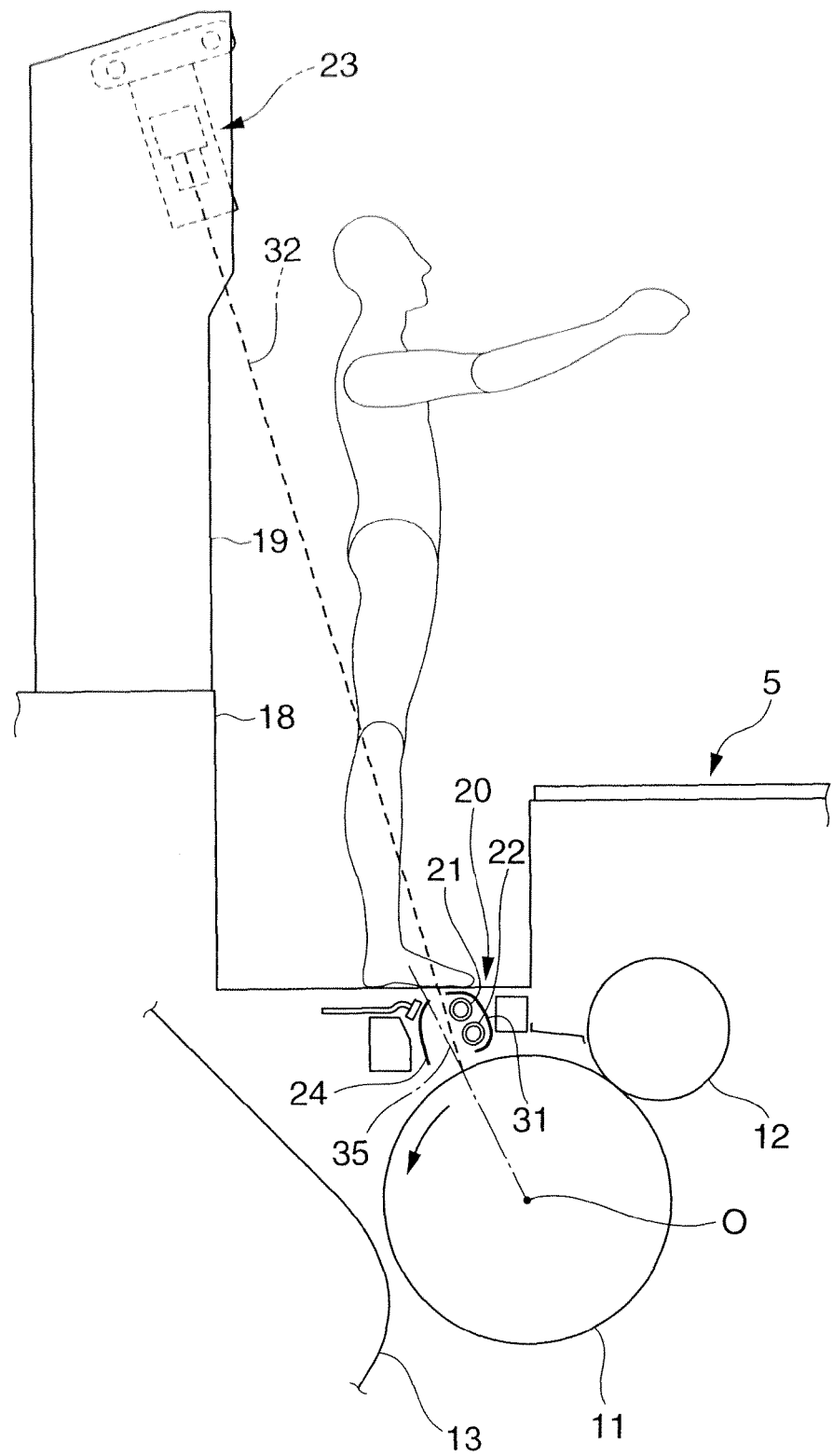
FIG. 2 is an enlarged view of a portion II in FIG. 1, which schematically shows a printing quality inspection apparatus according to the first embodiment of the present invention.

The coating unit 5 includes an impression cylinder (transport cylinder) 11 having a nickel-chromium film (specularly reflecting film) formed on its surface by a nickel-chromium process. A gripper device (not shown) which conveys the member to be printed 2 while holding its leading edge is provided in a portion which bisects the outer circumference of the impression cylinder 11. As shown in FIG. 2, a coater cylinder 12 is opposed to the impression cylinder 11, and varnish is supplied from a varnish supply device (not shown) onto the circumferential surface of the coater cylinder 12. The varnish is coated on the printing surface of the member to be printed 2 when the member to be printed 2 which is gripped and conveyed by the gripper device (not shown) passes through the gap between the impression cylinder 11 and the coater cylinder 12.

A delivery chain 13 extends across one sprocket (not shown) supported coaxially with a delivery cylinder which comes into contact with the impression cylinder 11, and the other sprocket (not shown) supported by the front end of the sheet delivery device 7. The delivery chain 13 includes a delivery gripper which transfers, by a gripping change, the member to be printed 2 which is gripped and conveyed by the gripper device of the impression cylinder 11.

With this configuration, the member to be printed 2 is supplied to a feeder board 15 by a sucker device (not shown) of the sheet feeding device 3. The member to be printed 2 is aligned in the longitudinal and widthwise directions by a stopper (not shown) and a side lay device (not shown) on the feeder board 15, and is then fed to the printing unit 4A via a swing arm shaft pregripper. The first color is printed by the printing unit 4A, and the second to sixth colors are sequentially printed by the printing units 4B to 4F, respectively. The member to be printed 2 undergoes varnish coating on its printing surface by the coating unit 5, and is conveyed by the delivery chain 13 to fall and is stacked on the delivery pile 6.

A printing quality inspection apparatus provided in the coating unit 5 will be described next.

Although the member to be printed 2 is conveyed while being attached on the surface of the impression cylinder 11 in practice, FIGS. 4 to 10 illustrate the member to be printed 2 while it is spaced apart from the surface of the impression cylinder 11, for the sake of descriptive convenience.

Figure 4:
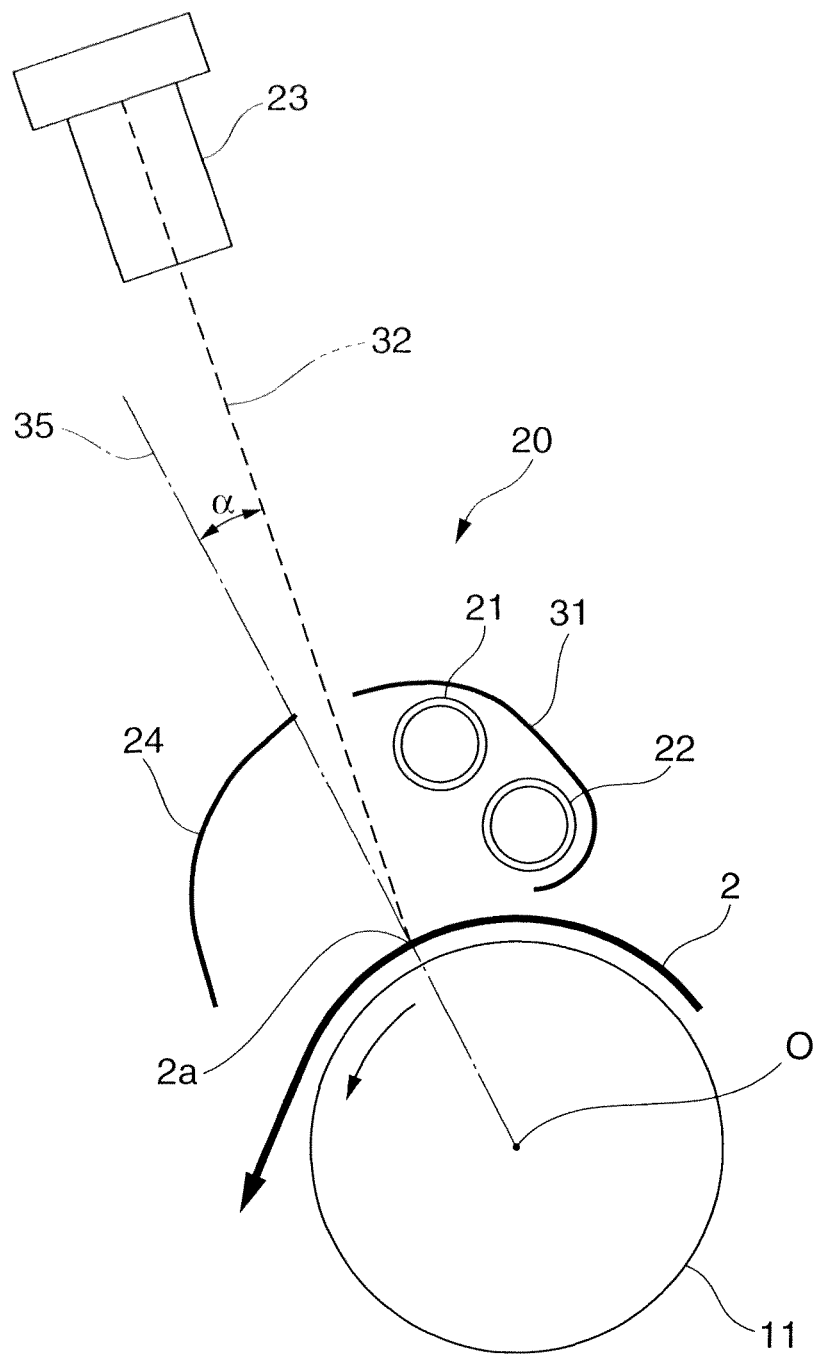
FIG. 4 is a side view of the printing quality inspection apparatus shown in FIG. 2.

A printing quality inspection apparatus 20 includes a pair of light sources (light irradiation devices) 21 and 22, a camera (image capture device) 23, a diffusely reflecting plate 24, and a determination device 25 (to be described later), as shown in FIG. 4. The light sources 21 and 22 irradiate an image printed on the member to be printed 2 with light. The camera 23 receives light which is emitted by the light sources 21 and 22 and reflected by the member to be printed 2, thereby capturing the image printed on the member to be printed 2. The diffusely reflecting plate 24 reflects the light from the light, sources 21 and 22 so that it uniformly scatters in multiple directions without luminance unevenness. The determination device 25 compares a detection signal from the camera 23 and a reference signal stored in advance to inspect the printing quality of the image printed on the member to be printed 2, based on the comparison result.

The light sources 21 and 22 use two fluorescent lamps extending in the cylinder axis direction of the impression cylinder 11. The camera 23 is attached to a mount 19 which stands upright on a frame 18, as shown in FIG. 2. The incident path on the camera 23 is set to be tilted by an angle α toward the upstream side in the direction, in which the member to be printed 2 is conveyed, with respect to a normal to the surface of the impression cylinder 11, which intersects with a tangent to this surface at right angles at an inspection position 2a (to be described later) defined on the impression cylinder 11. The diffusely reflecting plate 24 has an arcuated cross-section, and is arranged such that its inner surface faces the light sources 21 and 22 provided on the upstream side in the direction in which the member to be printed 2 is conveyed. The end of the diffusely reflecting plate 24 on the upstream side in the direction in which the member to be printed 2 is conveyed extends up to the position at which it comes into contact with the normal perpendicular to the tangent which, passes through the inspection position 2a. That is, the inspection position 2a is set to the position at which a line which connects the center of the impression cylinder 11 and the end of the diffusely reflecting plate 24 on the upstream side in the direction in which the member to be printed 2 is conveyed crosses over the member to be printed The members to be printed 2 to be inspected include vapor deposition paper (first sheet member) 2A having a specular surface on which a vapor deposition material such as aluminum is deposited, opaque paper (second sheet member) 2B which has a specularly reflecting surface and is available as a general printing sheet, and a transparent film (third sheet member) 2C which transmits light. Printing quality inspection apparatuses 20 having a common configuration inspect the qualities of images printed on these three types of members to be printed.

The light sources 21 and 22 are surrounded by a lamp house (light-shielding member) 31 which has a specularly reflecting surface as its inner surface and opens downstream in the direction (to be referred to as the paper conveyance direction hereinafter) in which the member to be printed 2 is conveyed. The lamp house 31 prevents the light from the light sources 21 and 22 from directly entering the camera 23, and diffusely reflects the light from the light sources 21 and 22 by its diffusely reflecting surface. The incident path on the camera 23 is set to pass through nearly the center of a cross-section of the gap formed between the end of the diffusely reflecting plate 24 on the upstream side in the paper conveyance direction and that of the lamp house 31 on the downstream side in the paper conveyance direction.

Figure 5:
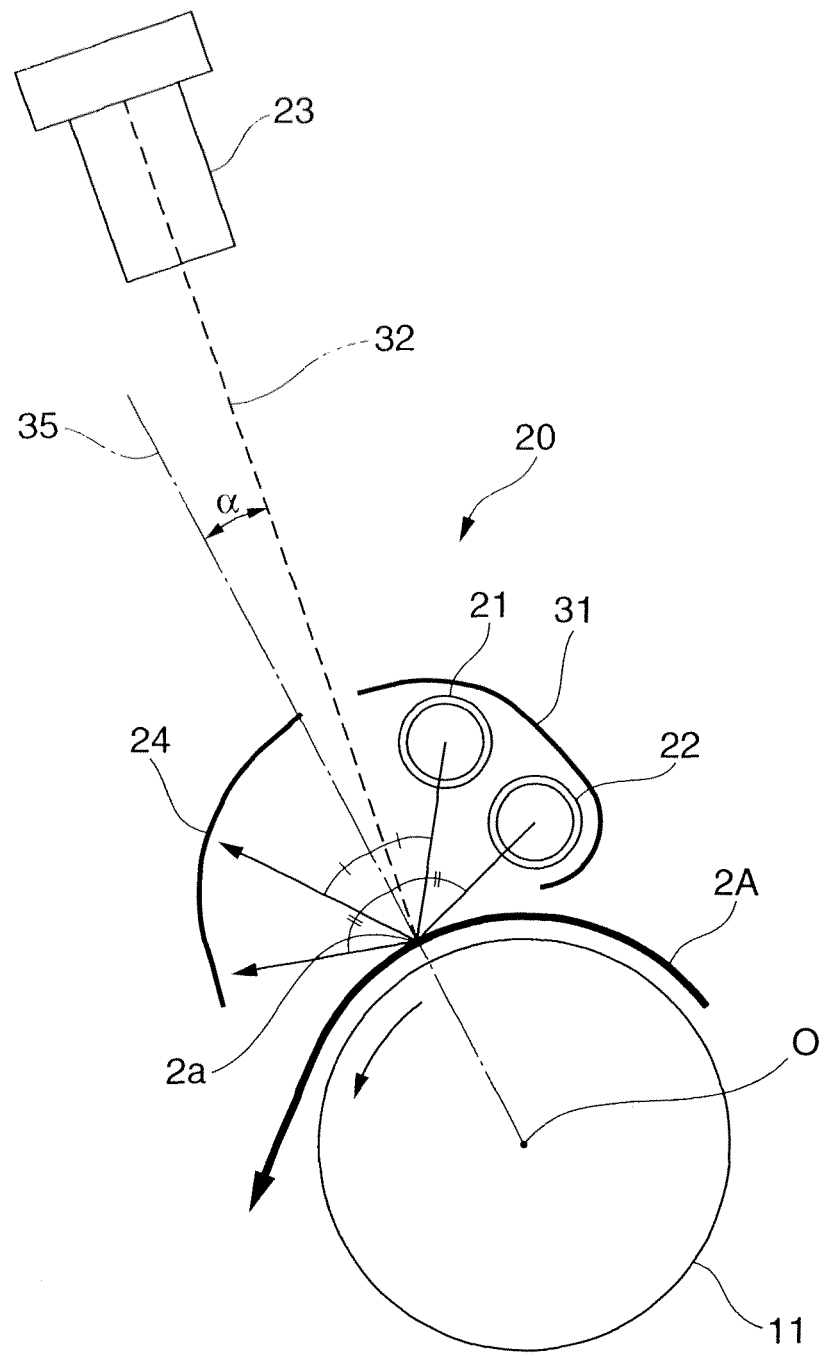
FIG. 5 is a side view showing the path of light which is emitted by a light source and specularly reflected by a member to be printed having a specular surface, and that of light which can enter a camera, in the printing quality inspection apparatus shown in FIG. 4.
Figure 6:
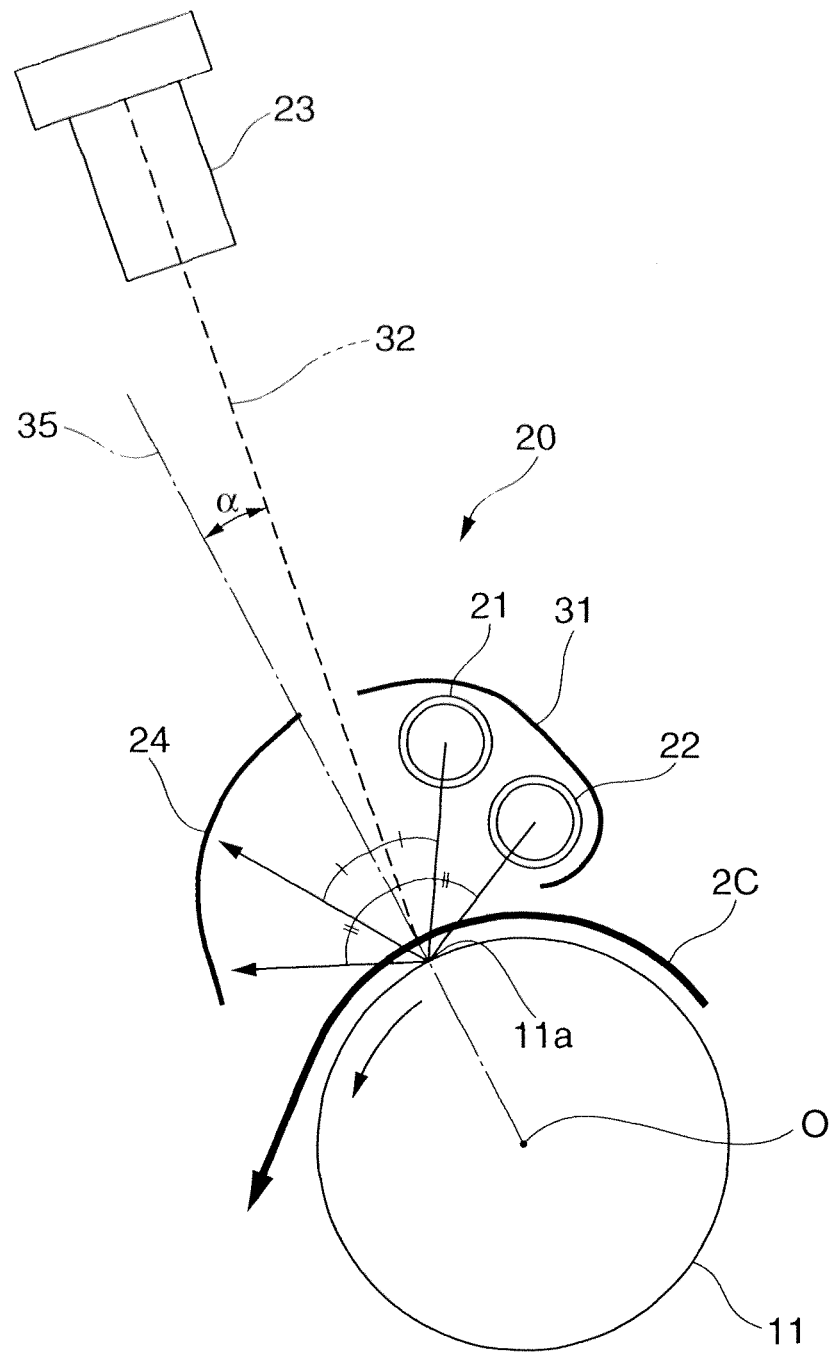
FIG. 6 is a side view showing the path of light which is emitted by the light source and specularly reflected by a transport cylinder surface, and that of light which can enter the camera, in the printing quality inspection apparatus shown in FIG. 4.

The light sources 21 and 22 are arranged at the positions at which light which is emitted by the light sources 21 and 22 and specularly reflected by the surface of the vapor deposition paper 2A does not directly enter the camera 23, as shown in FIG. 5. The light sources 21 and 22 are also arranged at the positions at which light which is emitted by the light sources 21 and 22 and specularly reflected by a surface 11a (the position at which this light intersects with the normal which passes through the inspection position 2a) of the impression cylinder 11 does not directly enter the camera 23, as shown in FIG. 6.

Figure 7:
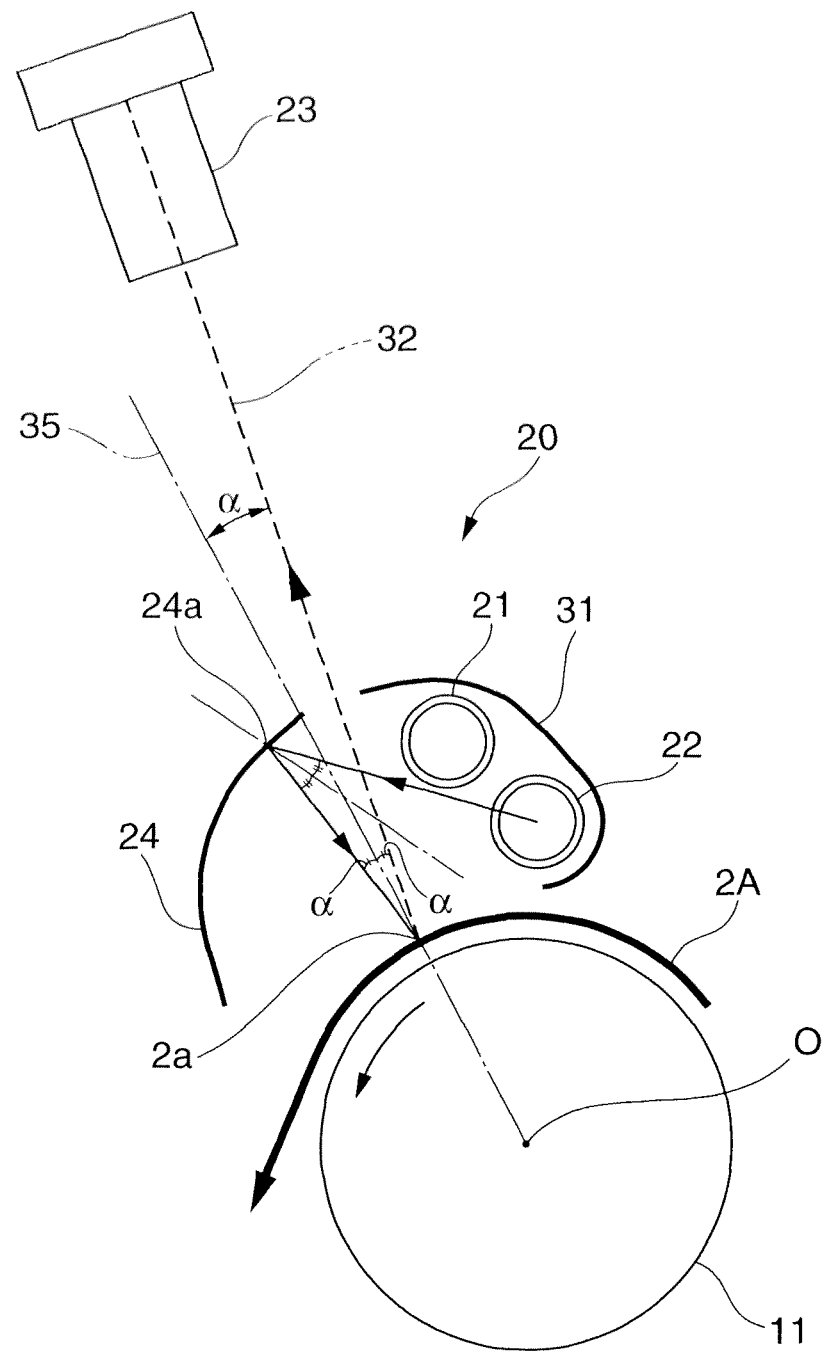
FIG. 7 is a side view showing the path along which light emitted by the light source enters the camera via a diffusely reflecting plate and vapor deposition paper, in the printing quality inspection apparatus shown in FIG. 4.

The camera 23 inspects the printing quality of the image on the member to be printed 2 at the inspection position 2a, as shown in FIG. 4. Light from the light sources 21 and 22 is reflected by the member to be printed 2 at the inspection position 2a, and enters the camera 23 via an incident path 32, thereby inspecting the printing quality. Hence, when the member to be printed 2 is the vapor deposition paper 2A, light from the light source 22 is diffusely reflected by the diffusely reflecting plate 24 at a reflection position 24a, is specularly reflected by the surface of the vapor deposition paper 2A at the inspection position 2a, and enters the camera 23 via the incident path 32, as shown in FIG. 7.

Figure 9:
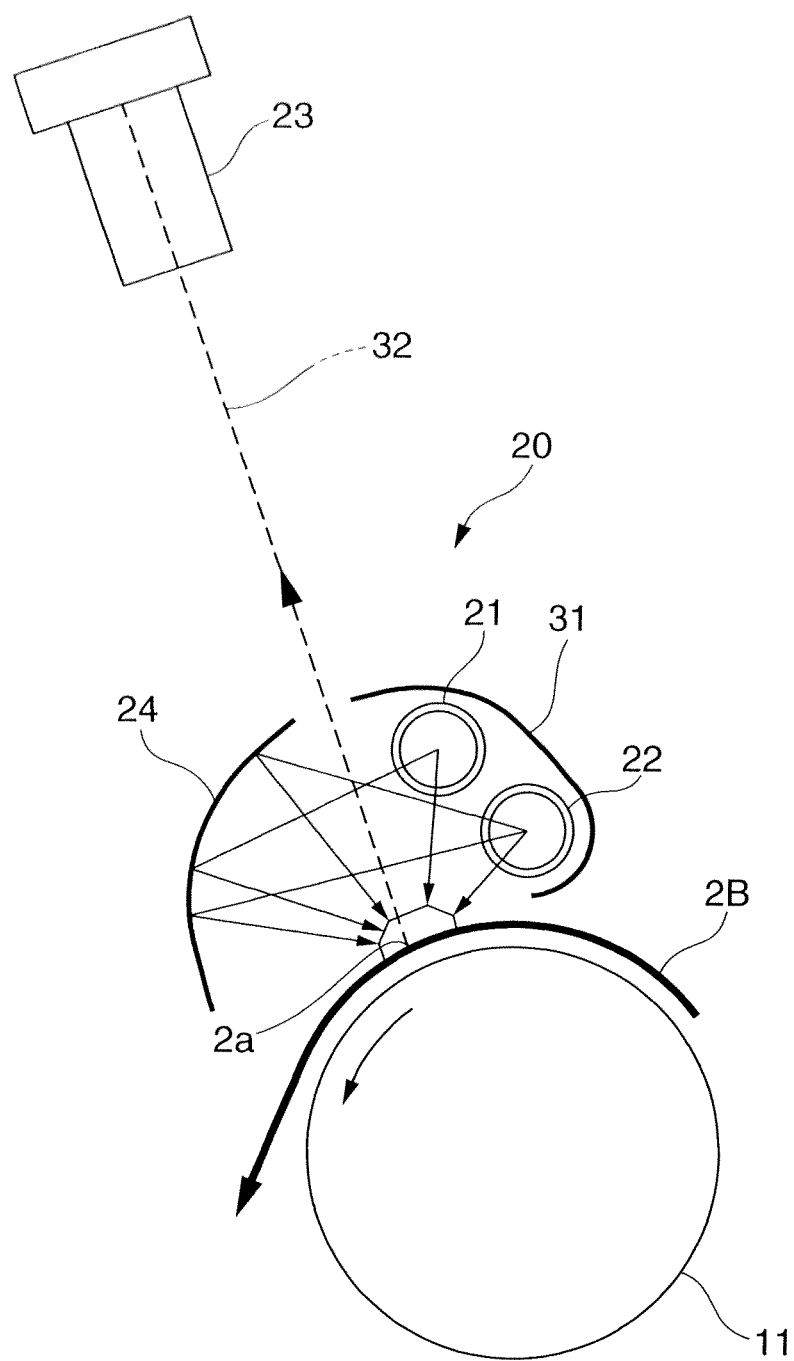
FIG. 9 is a side view showing the path along which light emitted by the light source enters the camera via the diffusely reflecting plate and opaque paper, in the printing quality inspection apparatus shown in FIG. 4.

When the member to be printed 2 is the opaque paper 2B, light from the light sources 21 and 22 enters the camera 23 via the following first and second paths, as shown in FIG. 9. In the first path, light from the light sources 21 and 22 is diffusely reflected by the surface of the opaque paper 2B at the inspection position 2a, and enters the camera 23 via the incident path 32. In the second path, light from the light sources 21 and 22 is reflected by the diffusely reflecting plate 24. A certain component of the diffusely reflected light is further diffusely reflected by the surface of the opaque paper 2B at the inspection position 2a, and enters the camera 23 via the incident path 32.

Figure 10:
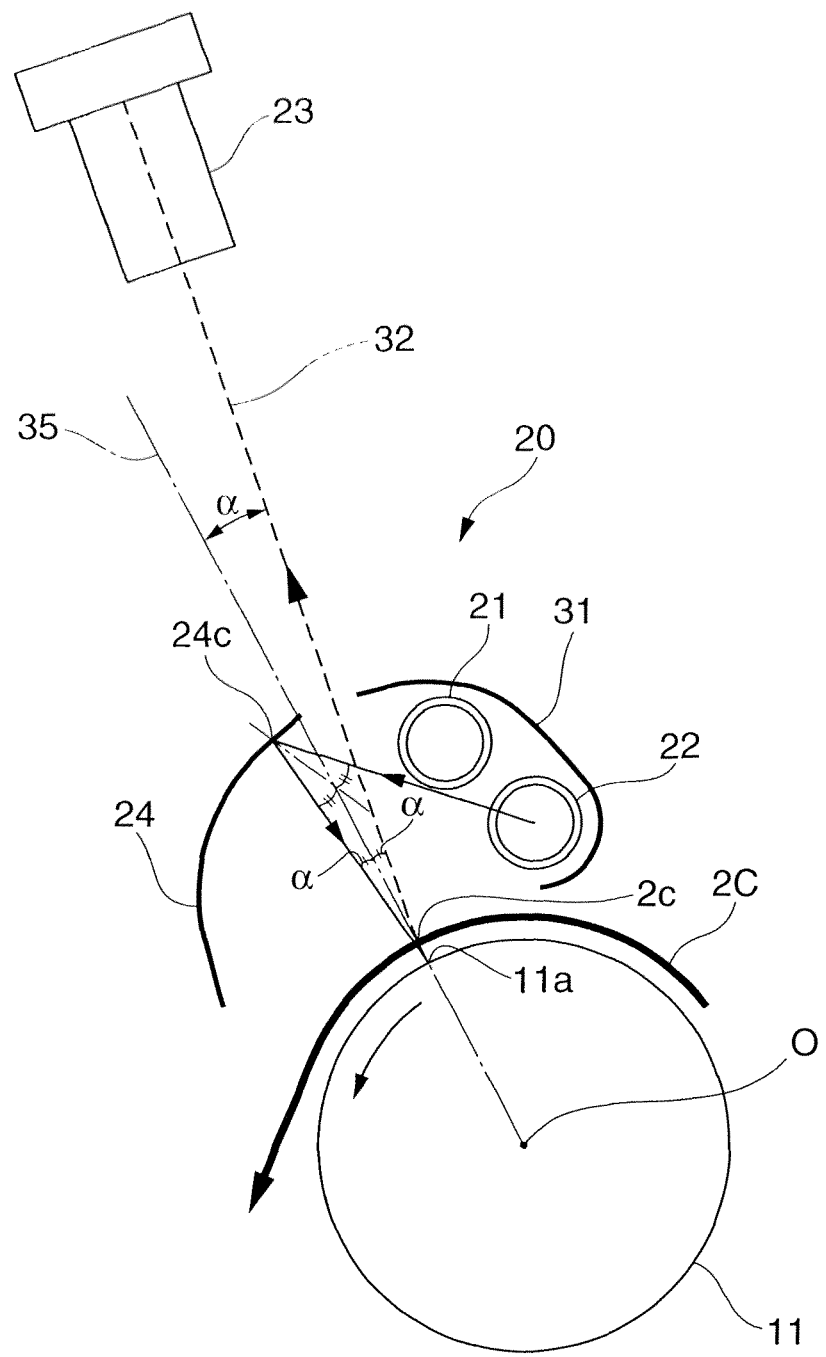
FIG. 10 is a side view showing the path along which light emitted by the light source enters the camera via the diffusely reflecting plate, a transparent film, and the transport cylinder surface (specular surface), in the printing quality inspection apparatus shown in FIG. 4.

When the member to be printed 2 is the transparent film 2C, light from the light source 22 is diffusely reflected by the diffusely reflecting plate 24 at a reflection position 24c, and transmitted through the transparent film 2C at an inspection position 2c, as shown in FIG. 10. The transmitted light is specularly reflected by the surface 11a of the impression cylinder 11, is transmitted through the transparent film 2C again, and enters the camera 23 via the incident path 32.

Note that as for light from the light source 22, light specularly reflected by the vapor deposition paper 2A, and that specularly reflected by the surface 11a of the impression cylinder 11 enter the camera 23 via the same incident path 32. On the other hand, light specularly reflected by the surface of the vapor deposition paper 2A, and that specularly reflected by the surface 11a of the impression cylinder 11 upon being transmitted through the transparent film 2C enter the camera 23 via paths which are different in length by the thickness of the transparent film 2C.

The light sources 21 and 22 are arranged on the upstream side in the paper conveyance direction with respect to a normal 35 (an extended line of a line which connects the center point O of the impression cylinder 11 and the inspection position 2a on the member to be printed 2 to each other) to the member to be printed 2 at the inspection position 2a, as shown in FIG. 4. On the other hand, the diffusely reflecting plate 24 is arranged on the downstream side in the direction, in which the member to be printed 2 is conveyed, with respect to the normal 35. That is, the diffusely reflecting plate 24 is opposed to the light sources 21 and 22 on the opposite side of the normal 35.

The diffusely reflecting plate 24 has a cross-section formed in an arcuated shape so that light which is emitted by the light sources 21 and 22 and reflected by the diffusely reflecting plate 24 focuses on the inspection position 2a on the member to be printed 2, as shown in FIG. 9. The arcuated cross-section of the diffusely reflecting plate 24 is formed so that its radius of curvature from the center point O of the impression cylinder 11 changes (increases toward the upstream side in the paper conveyance direction), as shown in FIG. 7.

Figure 8:
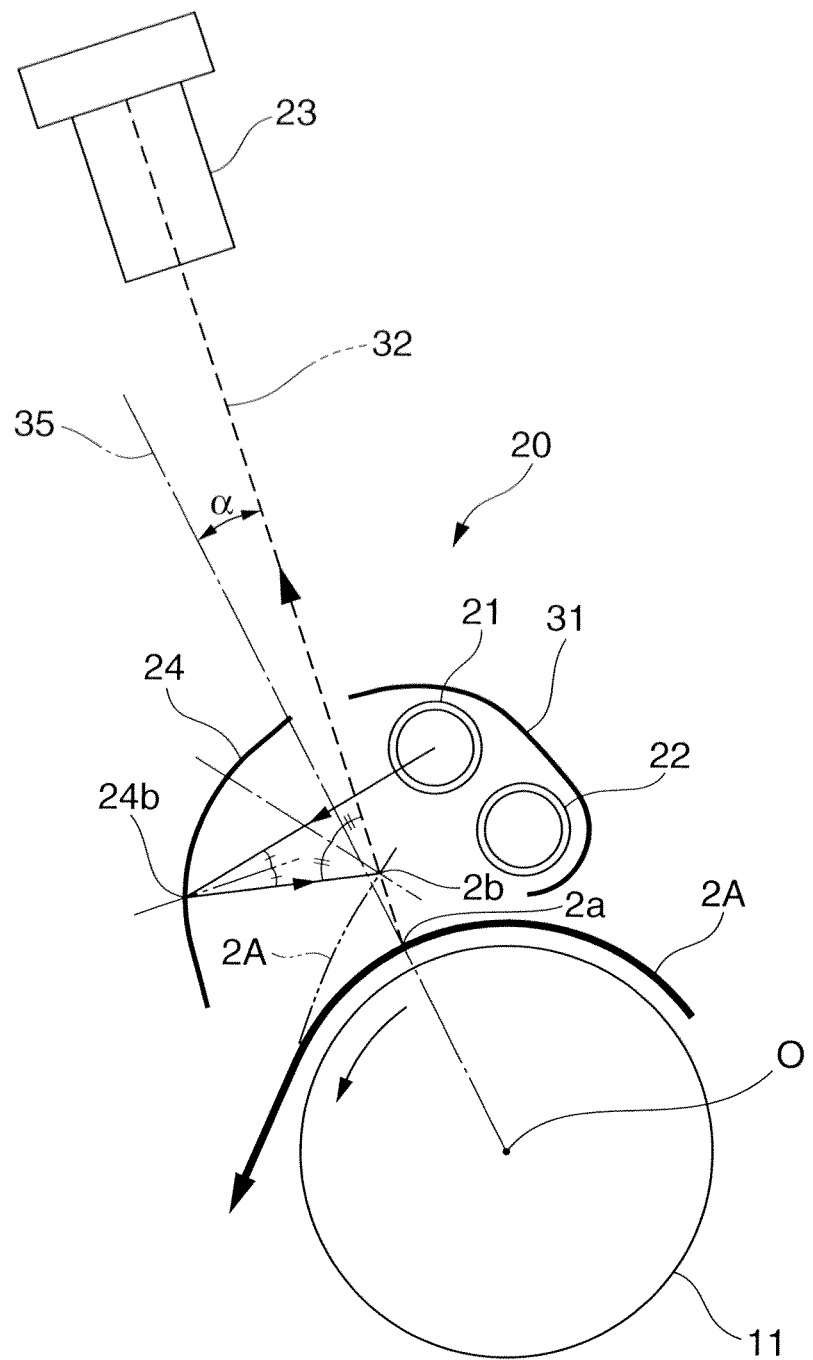
FIG. 8 is a side view for explaining the path along which light emitted by the light source enters the camera via the diffusely reflecting plate and vapor deposition paper when the vapor deposition paper shown in FIG. 7 floats or has a warpage.

Thus, light which is emitted by the light source 22 and reflected by the diffusely reflecting plate 24 at the reflection position 24a reaches the inspection position 2a on the member to be printed 2, and enters the camera 23 via the incident path 32. Also, light which is emitted by the light source 22 and reflected by the diffusely reflecting plate 24 at the reflection position 24c is specularly reflected by the surface 11a of the impression cylinder 11 upon being transmitted through the transparent film 2C at the inspection position 2c, and enters the camera 23 via the incident path 32, as shown in FIG. 10. Moreover, light which is emitted by the light source 21, and reflected by the diffusely reflecting plate 24 at a reflection position 24b impinges on a floating portion 2b on the vapor deposition paper 2A, and enters he camera 23 via the incident path 32, as shown in FIG. 8.

Figure 3:
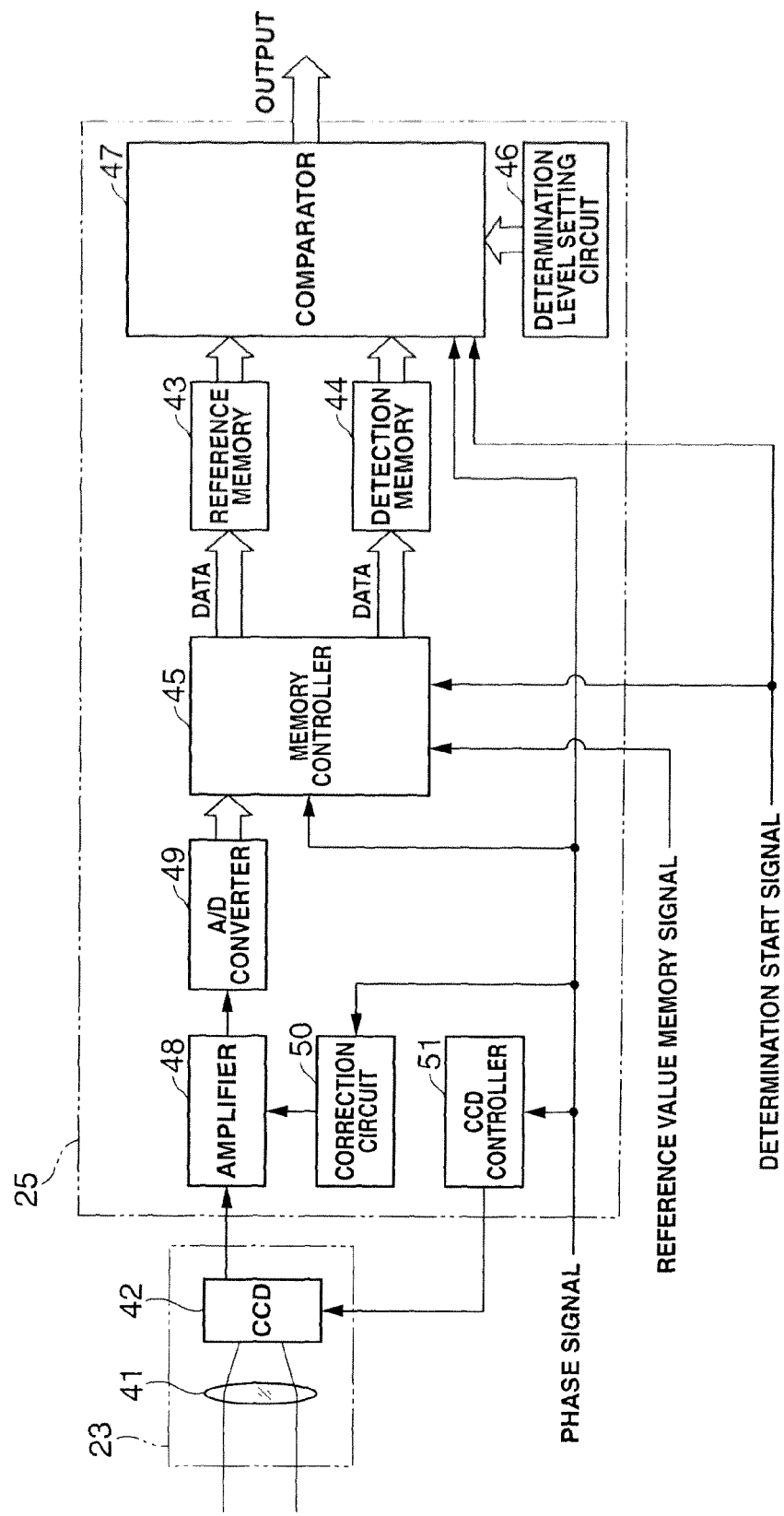
FIG. 3 is a block diagram showing the electrical configuration of the printing quality inspection apparatus shown in FIG. 2.

The optical/electrical configuration of the printing quality inspection apparatus according to this embodiment will be described next with reference to FIG. 3. The printing quality inspection apparatus includes the camera 23 which senses the image printed on the member to be printed 2, and the determination device 25 which inspects the printing quality of the image printed on the member to be printed 2, based on the image sensing output from the camera 23. The camera 23 includes an optical system including a lens 41, and a CCD (Charge Coupled Device) 42 which converts an image formed via the optical system into an electrical signal.

The determination device 25 includes a reference memory 43, detection memory 44, memory controller 45, determination level setting circuit 46, comparator 47, amplifier 48, A/D converter 49, correction circuit 50, and CCD controller 51. The reference memory 43 stores a reference image signal. The detection memory 44 stores a detection image signal. The memory controller 45 controls writing and reading of data into and from the reference memory 43 and detection memory 44. The determination level setting circuit 46 sets an allowable level difference between two signals read from the reference memory 43 and detection memory 44, respectively. The comparator 47 compares the two signals in consideration of the allowable level difference set by the determination level setting circuit 46. The amplifier 48 amplifies the output from the CCD 42. The A/D converter 49 analog-digital converts the output from the amplifier 48, and outputs the converted data to the memory controller 45. The correction circuit 50 adjusts the gain of the amplifier 48. The CCD controller 51 controls the CCD 42.

The reference memory 43 stores reference image data read from an image normally printed at the start of a printing job which uses one of the members to be printed 2 (vapor deposition paper 2A, opaque paper 2B, and transparent film 2C). Note that printing-job-specific reference image data are stored in the reference memory 43. The detection memory 44 stores detection image data read from the member to be printed 2 to be determined.

The memory controller 45 controls writing and reading of data into and from the reference memory 43 and detection memory 44. The determination level setting circuit 46 sets, in advance, an allowable level difference between reference image data read from the reference memory 43 and inspection image data read from the detection memory 44.

The comparator 47 outputs a signal indicating poor quality when the level difference between the reference image data and the inspection image data, which is output from the determination level setting circuit 46, is equal to or larger than the allowable level difference set by the determination level setting circuit 46. That is, the comparator 47 compares point by point reference image data and inspection image data corresponding to each pixel of the CCD 42 to compare the levels of these two data corresponding to this pixel, and outputs a failure signal if even one set of these data have a level difference equal to or larger than the allowable difference.

More specifically, the comparator 47 performs a first comparison operation of sequentially comparing, for each pixel, reference image data read from the reference memory 43 and inspection image data read from the detection memory 44. Next, the comparator 47 performs a second comparison operation of comparing the level difference between two signals obtained by the first comparison operation, and the allowable level difference output from the determination level setting circuit 46. If it is determined as a result of the second comparison operation that the level difference between the two signals is larger than the allowable level difference, the comparator 47 outputs a failure signal indicating that the image printed on the member to be printed 2 to be inspected has poor quality.

The correction circuit 50 adjusts the gain of the amplifier 48 in accordance with the rotational speed of the impression cylinder 11. That is, even if the same amount of light enters the camera 23, the output level of the CCD 42 reduces as the rotational speed of the impression cylinder 11 rises. Therefore, the amplifier 48 eliminates the influence of the rotational speed. A phase signal is supplied to the memory controller 45, comparator 47, correction circuit 50, and CCD controller 51. A reference value memory signal is supplied to the memory controller 45. A determination start signal is supplied to the memory controller 45 and comparator 47.

A phase signal is generated from a signal output from a rotary encoder (not shown) which detects the rotational phase of the impression cylinder 11. The phase signal includes a reference pulse which rises for every rotational operation of the impression cylinder 11, and a clock pulse which rises for every predetermined rotational operations of the impression cylinder 11. The reference value memory signal is a signal for reading reference image data into the reference memory 43 via the memory controller 45, and is supplied to the memory controller 45 by the operator's operation of a reference value memory switch (not shown). The determination start signal is a signal for instructing to start a comparison operation between reference image data and inspection image data, and is supplied to the memory controller 45 and comparator 47 by the operator's operation of a determination start switch (not shown).

With such a configuration, reference image data corresponding to a normal image printed on the member to be printed 2 is captured by a preprocess for a quality inspection process. First, the operator confirms the printing state of the member to be printed 2 during test printing using one of opaque paper, vapor deposition paper, and a transparent film. When it is confirmed that the printing state is good, the operator operates the reference value memory switch (not shown) to start supply of a reference value memory signal to the determination device 25 via the camera 23. When a reference signal indicating a reference position for the impression cylinder 11 is output from the rotary encoder, reference image data is captured from the member to be printed 2 held/conveyed by the impression cylinder 11, and is stored in the reference memory 43.

After reference image data of the member to be printed 2 held/conveyed by the impression cylinder 11 is stored in the reference memory 43, a determination process starts in response to a determination start signal. In this determination process, first, inspection image data, corresponding to the detection memory 44, of the member to be printed 2 held/conveyed by the impression cylinder 11 with rotation of the impression cylinder 11 is read, like reading of reference image data. Next, the inspection image data read at the time of the determination process, and the reference image data stored in advance are compared to determine whether a normal image is printed on the member to be printed 2, in accordance with whether the level values of the two data fall below the allowable level difference.

A inspection operation by the printing quality inspection apparatus 20 with the above-mentioned configuration will be described next with reference to FIGS. 5 to 10. A case in which the member to be printed 2 is the vapor deposition paper 2A will be explained first with reference to FIGS. 5, 7, and 8. In this case, light which is emitted by the light sources 21 and 22 and specularly reflected by the surface of the vapor deposition paper 2A held/conveyed by the impression cylinder 11 does not directly enter the camera 23, as shown in FIG. 5.

Light which is emitted by the light source 22 and reflected by the diffusely reflecting plate 24 at the reflection position 24a reaches the inspection position 2a on the vapor deposition paper 2A, as shown in FIG. 7. The light reflected by the vapor deposition paper 2A at the inspection position 2a enters the camera 23 via the incident path 32 which passes through the gap between the end of the diffusely reflecting plate 24 and that of the lamp house 31. At this time, if the inspection position 2a has no image, a full amount of light from the diffusely reflecting plate 24 enters the camera 23 intact. On the other hand, it the inspection position 2a has an image, a color corresponding to an ink color is absorbed by ink, so the amount of incident light decreases in proportion to the number of colors of pixels. The determination device 25 compares inspection image data captured by the camera 23, and reference image data of the vapor deposition paper 2A stored in the reference memory 43 in advance to determine the quality of the image printed on the vapor deposition paper 2A.

In this manner, in the case of the vapor deposition paper 2A, light which is emitted by the light sources 21 and 22 and specularly reflected by the surface of the vapor deposition paper 2A does not directly enter the camera 23, and only light diffusely reflected by the diffusely reflecting plate 24 is specularly reflected by the surface of the vapor deposition paper 2A, and enters the camera 23. Therefore, the quality of the image printed on the vapor deposition paper 2A can be inspected, as in the case of the opaque paper 2B.

A case in which the vapor deposition paper 2A flutters in the course of conveyance, so it floats from the surface of the impression cylinder 11 or it suffers from warpage will be explained next with reference to FIG. 8. Light which is emitted by the light source 21 and reflected by the diffusely reflecting plate 24 at the reflection position 24b is specularly reflected by the floating portion 2b of the vapor deposition paper 2A. The specularly reflected light enters the camera 23 via the incident path 32 without reaching the inspection position 2a.

At this time, light diffusely reflected by the diffusely reflecting plate 24 at the reflection position 24b impinges on the floating portion 2b of the vapor deposition paper 2A for the following reasons:

1) An arcuated cross-section of the diffusely reflecting plate 24 is formed so that its radius of curvature from the center point O of the impression cylinder 11 increases toward the upstream side in the paper conveyance direction.

2) The light sources 21 and 22 are arranged on the upstream side in the direction, in which the vapor deposition paper 2A is conveyed, with respect to the normal 35 to the vapor deposition paper 2A at the inspection position 2a.

3) The diffusely reflecting plate 24 is arranged on the downstream side in the direction, in which the vapor deposition paper 2A is conveyed, with respect to the normal 35.

4) The camera 23 is arranged on the upstream side in the direction, in which the vapor deposition paper 2A is conveyed, with respect to the normal 35.

For the above-mentioned reasons, even when the floating portion 2b or warpage occurs in the vapor deposition paper 2A, light which is diffusely reflected by the diffusely reflecting plate 24 and specularly reflected by the floating portion 2b or warped portion of the vapor deposition paper 2A reliably enters the camera 23. Therefore, the printing quality of the image printed on the vapor deposition paper 2A can reliably be inspected by the camera 23, regardless of the conveyance state of the vapor deposition paper 2A.

A case in which the member to be printed 2 is the opaque paper 2B will be explained next with reference to FIG. 9. For the sake of convenience, FIG. 9 shows the inspection position 2a in a polygonal shape to schematically represent the diffusely reflecting surface of the opaque paper 2B. Light which is emitted by the light sources 21 and 22 and diffusely reflected by the diffusely reflecting plate 24 reaches the inspection position 2a. The light diffusely reflected by the surface of the opaque paper 2B corresponding to the inspection position 2a enters the camera 23 via the incident path 32.

At this time, because the diffusely reflecting plate 24 is formed to have an arcuated cross-section, light which is emitted from the light sources 21 and 22 to the diffusely reflecting plate 24 focuses on the inspection position 2a, As a result, the amount of light incident on the camera 23 increases, and therefore never becomes insufficient. Similarly, a certain component of light which is directly guided from the light sources 21 and 22 to the inspection position 2a enters the camera 23 upon being diffusely reflected by the opaque paper 2B at the inspection position 2a, so the amount of light incident on the camera 23 increases.

If the inspection position 2a has no image, a full amount of light from the light sources 21 and 22 and diffusely reflecting plate 24 enters the camera 23 intact. On the other hand, if the inspection position 2a has an image, a color corresponding to an ink color is absorbed by ink, so the amount of incident light decreases. The determination device 25 compares inspection image data captured by the camera 23, and reference image data of the opaque paper 2B stored in the reference memory 43 in advance to determine the quality of the image printed on the opaque paper 2B.

A case in which the member to be printed 2 is the transparent film 2C will be explained next with reference to FIG. 10. Light which is emitted by the light sources 21 and 22 and diffusely reflected by the diffusely reflecting plate 24 at the reflection position 24c reaches the inspection position 2c on the transparent film 2C, as in the above-mentioned case of the vapor deposition paper 2A. If the inspection position 2c has no image, the irradiation light passes through the inspection position 2c while its amount remains the same. On the other hand, if the inspection position 2c has an image, light corresponding to an ink color is absorbed by ink, and passes through the inspection position 2c upon a decrease in amount. The light having passed through the inspection position 2c is specularly reflected by the surface 11a of the impression cylinder 11, is transmitted through the transparent film 2C again, and enters the camera 23 via the incident path 32. The light incident on the camera 23 is converted into inspection image data by the determination device 25, and the inspection image data and reference image data of the transparent film 2C stored in the reference memory 43 in advance are compared by the determination level setting circuit 46. The printing quality of the image printed on the transparent film 2C is determined in accordance with the output from the determination level setting circuit 46.

According to this embodiment, the quality of the image printed on the transparent film 2C can automatically be determined without requiring the operator to extract printed transparent films 2C for every predetermined number of sheets and visually inspect the images printed on them. Therefore, it is possible not only to relieve the operator's burden but also to prevent the waste of printing materials. Also, no printing failure occurs while the operator extracts and inspects a printing product, thus making it possible to avoid the trouble that a defective printing product is shipped. In this case, defective printing products are not, produced in large quantities, thus preventing the waste of printing materials.

Figure 11:
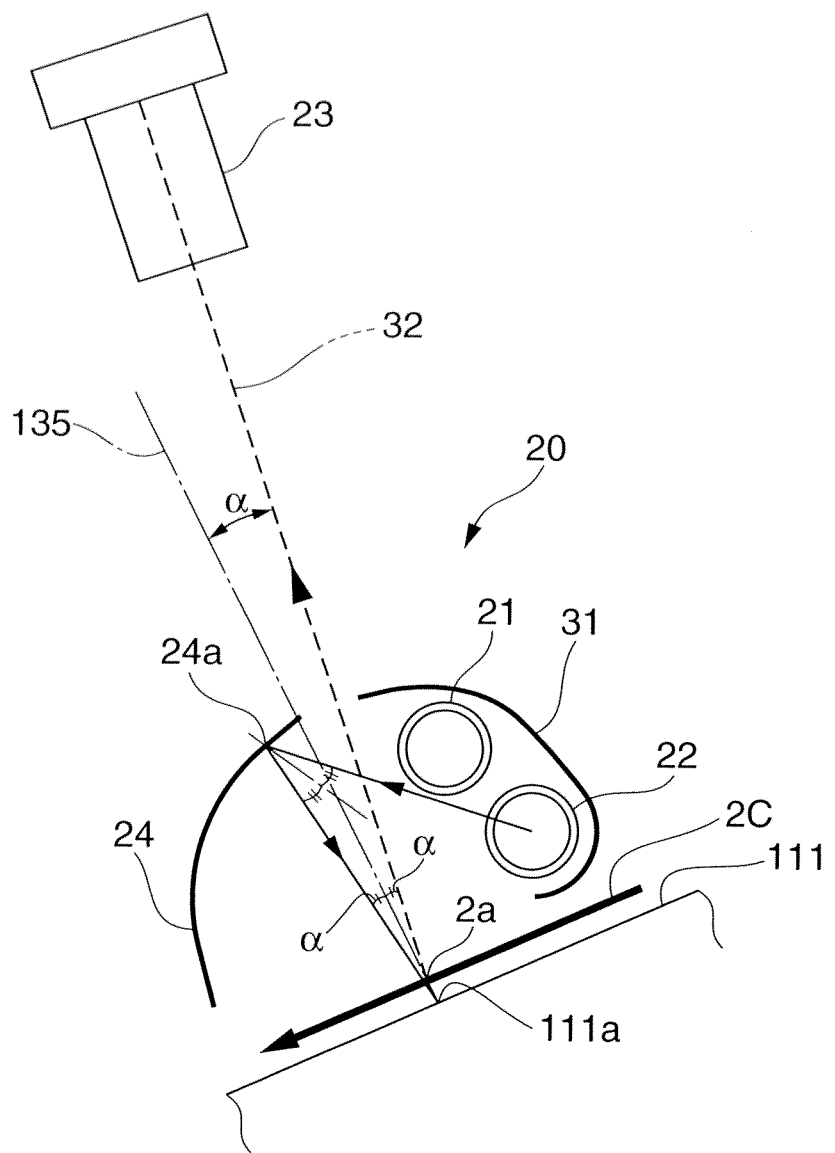
FIG. 11 is a side view of a printing quality inspection apparatus according to the second embodiment of the present invention.

The second embodiment of the present invention will be described next with reference to FIG. 11. The same reference numerals as in the above-described first embodiment denote the same members in FIG. 11, and a detailed description thereof will not be given.

The second embodiment is different from the first embodiment in that a transparent film 2C is, for example, gripped and conveyed by a gripper device of a delivery chain 13, instead of being conveyed by a cylinder. In the second embodiment, the transparent film 2C is conveyed along a rectilinear path, so a specularly reflecting member 111 is arranged such that its surface 111a becomes parallel to the conveyance path of a member to be printed. In this case, the transparent film 2C which passes through an inspection point 2a is inspected in a flat state without forming a curved surface. With such a configuration, light which is emitted by light sources 21 and 22 and passes through the inspection point 2a on the transparent film 2C is reflected by the surface 111a of the specularly reflecting member 111, and enters a camera 23 upon passing through the inspection point 2a again.

Although the two light sources 21 and 22 are used as illumination devices in the above-described embodiments, only one light source may be used as long as a sufficient amount of light can be obtained, or three or more light sources may be used as needed.

As has been described above, according to the present invention, the common apparatus can inspect the printing qualities of images of printing products printed on three types of members to be printed, so its manufacturing cost can be reduced. Also, in inspecting the printing quality of an image printed on a member to be printed, the operator need not operate a selection switch used to select the type of member to be printed, thus relieving the operator's burden. Moreover, neither erroneous detection nor erroneous determination that occurs if the operator has forgotten to operate the selection switch happens, thus making it possible to prevent waste of printing materials.

Even if the vapor deposition paper flutters in the course of conveyance, and therefore floats from the transport cylinder or suffers from warpage, light diffusely reflected by the diffusely reflecting plate impinges on the floating portion or warpage of the member to be printed, thereby allowing inspection.

What is claimed is:

1. A printing quality inspection apparatus including
a light irradiation device which irradiates with light at an inspection position on a member to be printed including a second sheet member having an image printed thereon and a diffusely reflecting surface, and a first sheet member having an image printed thereon and a specularly reflecting surface,
an image capture device which receives light which is emitted by the light irradiation device and passes through the member to be printed, thereby capturing the image on the member to be printed,
a diffusely reflecting plate which diffuses and reflects incident light opposed to the light irradiation device on an opposite side of a light incident path defined from the member to be printed to the image capture device, and
a determination device which compares an image capture signal output from the image capture device and a reference signal stored in advance to inspect quality of the image printed on the member to be printed, wherein
when the member to be printed is the second sheet member, the light emitted by the light irradiation device is diffusely reflected by the second sheet member and enters the image capture device, and
when the member to be printed is the first sheet member, the light emitted by the light irradiation device is, after diffusely reflected by the diffusely reflecting plate, specularly reflected by the first sheet member and enters the image capture device, wherein
the image capture device is arranged at an upper position on an upstream side with respect to the inspection position in a conveyance direction of the member,
the light irradiation device is arranged at an upper position further along the upstream side with respect to the image capture device in a conveyance direction of the member,
the diffusely reflecting plate is arranged at an upper position on a downstream side with respect to the inspection position in a conveyance direction of the member and
the light incident path defined from inspection position to the image capture device is set to be tilted by a predetermined angle toward the upstream side with respect to a direction perpendicular to the conveyance direction of the member.

2. An apparatus according to claim 1, wherein
the diffusely reflecting plate is formed to have an arcuated cross-section while an inner surface thereof faces the light irradiation device.

3. An apparatus according to claim 1, further comprising a transport cylinder which holds and conveys the member to be printed,
wherein the image capture device captures the image on the member to be printed when the member to be printed is transported by said transport cylinder.

4. An apparatus according to claim 3, wherein
the member to be printed includes a transparent, third sheet member having an image printed thereon, in addition to the first sheet member and the second sheet member,
said transport cylinder has a specularly reflecting film formed on a surface thereof,
the diffusely reflecting plate is formed to have an arcuated cross-section, a radius of curvature from the center of said transport cylinder of which changes gradually, while an inner surface thereof faces the light irradiation device, and
when the member to be printed is the third sheet member, the light emitted by the light irradiation device is transmitted through the third sheet member after diffusely reflected by the diffusely reflecting plate, subsequently specularly reflected by the specularly reflecting film on said transport cylinder, and enters the image capture device.

5. An apparatus according to claim 1, further comprising a light-shielding member which is arranged between the light irradiation device and the image capture device, and prevents the light from the light irradiation device from directly entering the image capture device.

6. An apparatus according to claim 5, wherein
said light-shielding member is a lamp house which is formed in an arcuated shape so as to cover the light irradiation device, and has a diffusely reflecting surface as an inner surface thereof.

7. A printing quality inspection apparatus including
a light irradiation device which irradiates a transparent sheet member having an image printed thereon with light,
an image capture device which receives light which is emitted by the light irradiation device and passes through the transparent sheet member, thereby capturing the image on the transparent sheet member,
a determination device which compares an image capture signal output from the image capture device and a reference signal stored in advance to inspect quality of the image printed on the transparent sheet member,
a diffusely reflecting plate which diffuses and reflects incident light opposed to the light irradiation device on an opposite side of a light incident path defined from the member to be printed to the image capture device, and
one of a specularly reflecting film and a specularly reflecting member which is provided at an opposite side of the image capture device with respect to a conveyance path of the transparent sheet member, wherein
the light emitted by the light irradiation device passes through the transparent sheet member upon being diffusely reflected by the diffusely reflecting plate, is specularly reflected by one of the specularly reflecting film and the specularly reflecting member, and enters the image capture device,
the image capture device is arranged at an upper position on an upstream side with respect to an inspection position in a conveyance direction of the member to be printed,
the light irradiation device is arranged at an upper position further along the upstream side with respect to the image capture device in the conveyance direction of the member to be printed, and
the diffusely reflecting plate is arranged at an upper position on a downstream side with respect to the inspection position in a conveyance direction of the member to be printed.

8. An apparatus according to claim 7, further comprising a light-shielding member which is arranged between the light irradiation device and the image capture device, and prevents the light from the light irradiation device from directly entering the image capture device.

9. An apparatus according to claim 8, wherein said light-shielding member is a lamp house which is formed in an arcuated shape so as to cover the light irradiation device, and has a diffusely reflecting surface as an inner surface thereof.

\* \* \* \* \*